US00PP35332P2

(12) United States Plant Patent
Batson

(10) Patent No.: US PP35,332 P2
(45) Date of Patent: Aug. 22, 2023

(54) ***HIBISCUS* PLANT NAMED 'GFNHSRP'**

(50) Latin Name: *Hibiscus syriacus*
Varietal Denomination: GFNHSRP

(71) Applicant: Daniel Batson, Perkinston, MS (US)

(72) Inventor: Daniel Batson, Perkinston, MS (US)

( * ) Notice: Subject to any disclaimer, the term of this patent is extended or adjusted under 35 U.S.C. 154(b) by 0 days.

(21) Appl. No.: 18/087,286

(22) Filed: Dec. 22, 2022

(51) Int. Cl.
*A01H 5/02* (2018.01)
*A01H 6/60* (2018.01)

(52) U.S. Cl.
USPC ..... Plt./257
CPC ..... *A01H 6/608* (2018.05)

(58) Field of Classification Search
USPC ..... Plt./257
CPC ..... A01H 6/608; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Hibiscus* plant named 'GFNHSRP' is disclosed, characterized by reddish-pink colored flowers with a large, deep red "eye". Plants have upright, columnar, narrow habits. The new variety is a *Hibiscus*, typically produced as an ornamental plant.

2 Drawing Sheets

Latin name of the genus and species: *Hibiscus syriacus*. Variety denomination: 'GFNHSRP'.

BACKGROUND OF THE INVENTION

The new *Hibiscus* cultivar is a product of a naturally occurring branch mutation of the variety *Hibiscus syriacus* 'Gandini van Aart', U.S. Plant Pat. No. 28,892. The new cultivar was found and selected by the inventor in the summer of 2018 in Stone County, Miss.

Asexual reproduction of the new cultivar 'GFNHSRP' was first performed in the summer of 2019 in Stone County, Miss., by softwood cuttings. Subsequent propagation has shown that the unique features of this cultivar are stable and reproduced true to type in successive generations.

Date of first sale was Jun. 21, 2022, occurring in Grand Haven, Mich. This sale was made directly by the inventor or one who obtained the claimed invention directly or indirectly from the inventor. This sale and all public disclosures made between Jun. 21, 2022, and the filing of this application fall within the exception allowed under 102(b)(1).

SUMMARY OF THE INVENTION

The cultivar 'GFNHSRP' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'GFNHSRP'. These characteristics in combination distinguish 'GFNHSRP' as a new and distinct *Hibiscus* cultivar:

1. Reddish-pink colored flowers with a large, deep red "eye".
2. "Eye" of flower extends to around 50% of each petal surface.
3. Upright and columnar/narrow habit.

PARENT COMPARISON

Plants of the new cultivar 'GFNHSRP' are similar to the seed parent *Hibiscus* 'Gandini van Aart', in most horticultural characteristics. However, characteristics of the new cultivar differ in the following:

1. Flowers of the new variety are reddish-pink with a large, deep red "eye". Flowers of the seed parent are pure white.

COMMERCIAL COMPARISON

Plants of 'GFNHSRP' are similar in some horticultural characteristics to the variety *Hibiscus* 'Gandini Santiago', U.S. Plant Pat. No. 25,568. The new variety, however, differs in the following:

1. Flowers of the new variety are darker reddish-pink with a large, deep red "eye". Flowers of this comparator are lighter, purplish-pink with a large, deep-red "eye."

BRIEF DESCRIPTION OF THE PHOTOGRAPHS

Figure 1:
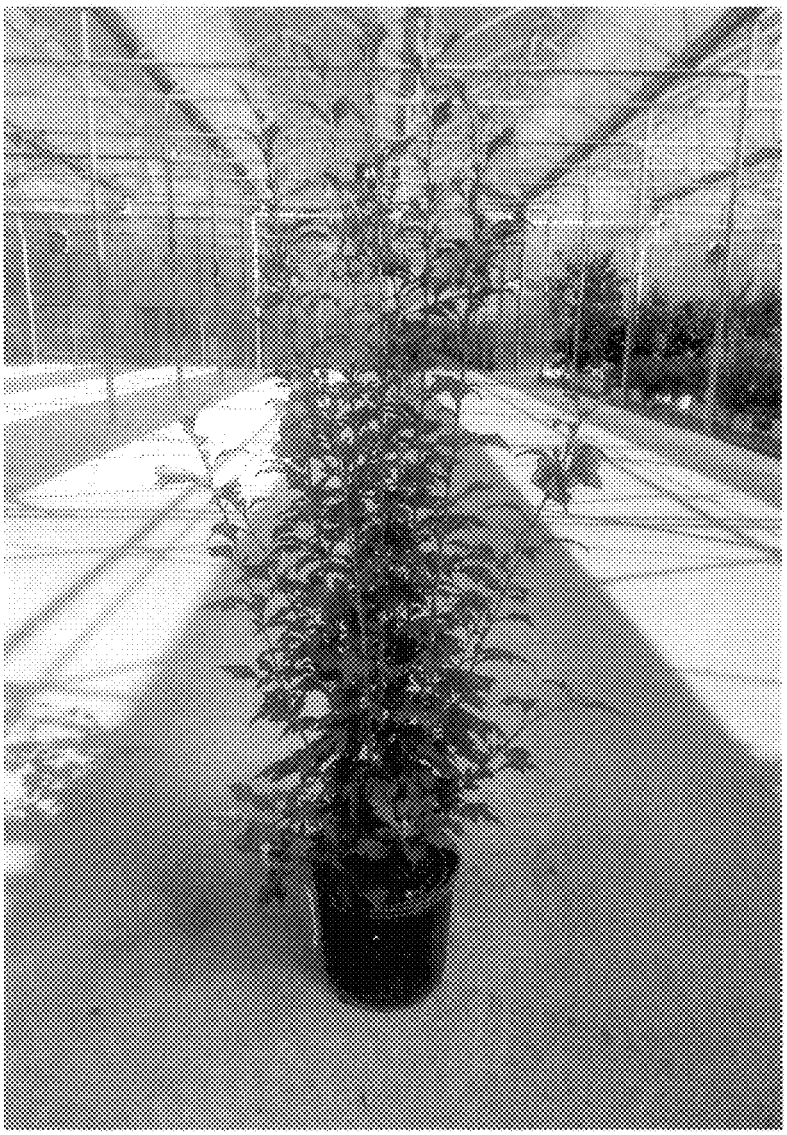

The accompanying photograph in FIG. 1 illustrates in full color a typical plant of 'GFNHSRP' grown outdoors at a commercial nursery in Grand Haven, Mich. This plant is approximately 3 years old, shown in a 3-gallon container.

Figure 2:
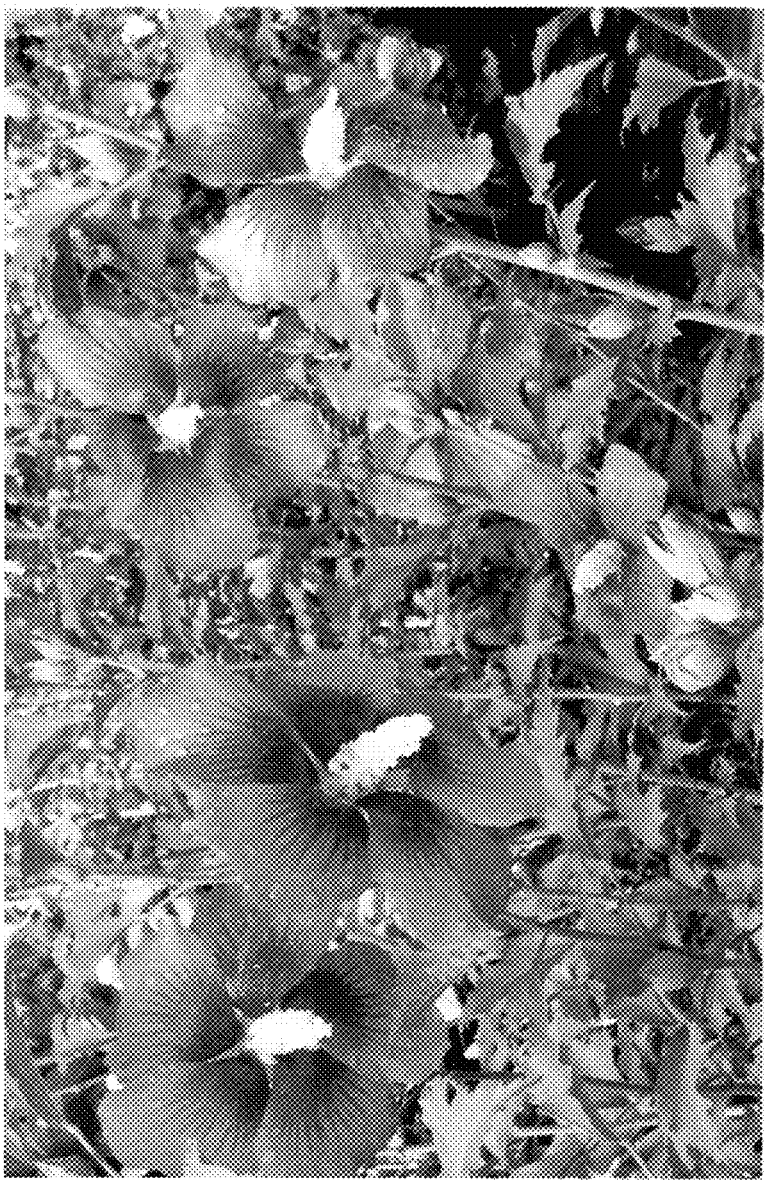

FIG. 2 illustrates a closer view of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe a 'GFNHSRP' plant. This plant is approximately 3 years old, grown in a 3-gallon container. Temperatures ranged from 5° C. to 10° C. at night and 18° C. to 27° C. during the day. No artificial light, photoperiodic treatments were given to the plants. Measurements and numerical values represent averages of typical plant types.

Botanical classification: *Hibiscus syriacus* 'GFNHSRP'.

PROPAGATION

Time to initiate roots: 6 weeks at 18° C.-27° C.

Time to produce a rooted plant: 3 months.

Root description: Fibrous, medium root thickness. Moderate branching and density. Tan/brown in color, not effectively measured with a color chart.

PLANT

Plant type: Perennial flowering shrub.

Age of plant described: 3 years old.

Growth habit: Predominately upright.

Plant vigor: Moderate.

Height: 110 cm.

Plant spread: 50 cm.

Branching characteristics: Basal, pinching required.

Quantity of lateral branches: About 20.

Characteristics of primary lateral branches:

*Length.*—100 cm.

*Diameter.*—5 mm.

*Shape.*—Rounded.

*Aspect.*—70-90°.

*Strength.*—Strong.

*Color.*—New growth: RHS Yellow-Green 144A. Mature growth: Near RHS Grey-Brown 199D.

*Pubescence.*—Some, slight, on newer growth only.

Internode length: 4.5 cm.

FOLIAGE

Leaf:

*Arrangement.*—Alternate, single.

*Average length.*—6 cm.

*Average width.*—3.5 cm.

*Shape of blade.*—Oblanceolate.

*Apex.*—Acute to acuminate.

*Base.*—Cuneate.

*Margin.*—Serrate.

*Texture of top surface.*—Glabrous with prominent veining.

*Texture of bottom surface.*—Glabrous with prominent veining.

*Color.*—Young foliage upper side: RHS Green 137B. Young foliage under side: RHS Yellow-Green 144A. Mature foliage upper side: RHS Green 137B. Mature foliage under side: RHS Yellow-Green 144D.

*Venation.*—Type: Pinnate. Venation color, upper side: RHS Green 138B. Venation color, under side: RHS Yellow-Green 144D.

*Petiole.*—Length: 2 cm. Diameter: 1 mm. Color: RHS Green 137B. Texture: Lightly pubescent.

FLOWER

Natural flowering season: Mid to late summer.

Flower type and habit: Single flowers arranged at terminal ends of lateral branches in groups of 2 to 4, with some flowers emerging occasionally at leaf internodes slightly below branch apex.

Quantity of flowers per lateral stem: 2 to 4.

Quantity of buds per lateral stem: About 10.

Quantity of flowers and buds per lateral stem: Average range 600 to 800.

Persistent or self-cleaning: Persistent.

Fragrance: None.

Bud:

*Shape.*—Ovate.

*Length.*—1.5 cm.

*Diameter.*—1 cm.

*Color.*—RHS Green 138B.

Flower:

*Shape.*—Round, single whorl.

*Length.*—10 to 11 cm.

*Diameter.*—10 to 11 cm.

*Depth.*—5 cm.

*Aspect.*—Upright and outward.

Petals:

*Quantity.*—5.

*Arrangement.*—Whorl.

*Length.*—5.5 cm.

*Width.*—4.5 cm.

*Shape.*—Obovate to orbicular.

*Apex.*—Obtuse.

*Base.*—Cuneate.

*Margin.*—Slightly crenate with fine ciliate hairs near base only.

*Texture, upper and lower surfaces.*—Soft and silky.

*Color.*—When opening, upper surface: RHS Greyed-Purple 186C with a large Greyed-Purple 183B "eye" encompassing 50% of the petal surface; the "eye" has feathered margins. When opening, lower surface: RHS Greyed-Purple 183B with some Greyed-Purple 185A near base. Fully opened, upper surface: RHS Greyed-Purple 186C with a large Greyed-Purple 183B "eye" encompassing 50% of the petal surface; the "eye" has feathered margins. Fully opened, lower surface: RHS Greyed-Purple 183B with some Greyed-Purple 185A near base.

Sepals:

*Appearance.*—Triangular shaped, fused at base, with additional linear structures arranged in a whorl beneath main sepals.

*Arrangement.*—Whorl.

*Quantity.*—5 main sepals with 5 additional linear extensions.

*Length.*—Main: 1.25 cm. Secondary: 1 cm.

*Width.*—Main: 16 mm. Secondary: 1 mm.

*Shape.*—Main: Triangular. Secondary: Linear.

*Margin.*—Entire.

*Apex.*—Acute.

*Base.*—Fused.

*Color.*—Upper side: Main: RHS Green 138B. Secondary: RHS Yellow-Green 146A. Under side: Main: RHS Green 138B. Secondary: RHS Yellow-Green 146A.

*Texture.*—Upper side: Somewhat coarse with small, textured bumps. Under side: Smooth, glabrous.

Calyx:

*Shape.*—Collar-like.

*Length.*—2 cm.

*Width.*—1.5 cm.

Peduncle:

*Length.*—2.5 cm.

*Diameter.*—3 mm.

*Angle.*—15° to 45°.

*Strength.*—Good.

*Texture*.—Lightly pubescent.
*Color*.—RHS Yellow-Green 146A.

REPRODUCTIVE ORGANS

Stamens:
*Number*.—About 75.
*Filament length*.—3 mm.
*Filament color*.—RHS White NN155B.
Anthers:
*Shape*.—Rounded.
*Length*.—1 mm.
*Color*.—RHS Yellow 4D.
*Pollen color*.—RHS Yellow 4D.
*Pollen amount*.—Abundant.
Pistil:
*Arrangement*.—Pistil fused, 5 protruding stigma from top.
*Number*.—1.
*Length*.—4 cm.
*Style*.—Length: 3.5 cm. Color: RHS White NN155B.
*Stigma*.—Shape: Peltate. Color: RHS White NN155B.

OTHER CHARACTERISTICS

Seeds: Not observed.
Disease/pest resistance: Neither other resistance nor susceptibility to normal diseases and pests of *Hibiscus syriacus* have been observed.
Temperature tolerance: Low temperature tolerance to −31° C., high temperature tolerance to at least 38° C.

What is claimed is:

1. A new and distinct cultivar of *Hibiscus* plant named 'GFNHSRP' as herein illustrated and described.

* * * * *